United States Patent [19]

Muller

[11] Patent Number: 4,899,762
[45] Date of Patent: Feb. 13, 1990

[54] MULTI-PURPOSE INTEGRATED SURGICAL DRAPE, DRESSING, AND CLOSURE STRUCTURE AND METHOD

[75] Inventor: George H. Muller, Ann Arbor, Mich.

[73] Assignee: Detroit Neurosurgical Foundation, Detroit, Mich.

[21] Appl. No.: 79,498

[22] Filed: Jul. 30, 1987

Related U.S. Application Data

[63] Continuation-in-part of Ser. No. 444,842, Nov. 26, 1982, abandoned, which is a continuation-in-part of Ser. No. 178,103, Aug. 14, 1980, abandoned.

[51] Int. Cl.$^4$ ............................................. A61F 13/00
[52] U.S. Cl. ..................................... 128/850; 128/854
[58] Field of Search ................... 128/132 D, 156, 335, 128/155, 849-855

[56] References Cited

U.S. PATENT DOCUMENTS

| | | | |
|---|---|---|---|
| 3,698,395 | 10/1972 | Hasson | 128/335 |
| 3,783,862 | 1/1974 | Schrading et al. | 128/132 D |
| 3,903,882 | 9/1975 | Augurt | 128/156 |
| 3,908,650 | 9/1975 | Dunshee et al. | 128/156 |
| 4,095,595 | 6/1978 | Stanford | 128/156 |
| 4,114,624 | 9/1978 | Haverstock | 128/335 |
| 4,153,055 | 5/1979 | Etes | 128/156 |
| 4,281,650 | 8/1981 | Spiegelberg | 128/156 |
| 4,373,519 | 2/1983 | Errede et al. | 128/156 |
| 4,524,767 | 6/1985 | Glassman | 128/132 D |
| 4,625,720 | 12/1986 | Lock | 128/132 D |

*Primary Examiner*—Robert A. Hafer
*Assistant Examiner*—Michael Brown

[57] ABSTRACT

Combination surgical drape, dressing and closure structure and method of use before, during and after a surgical procedure. A combination drape and dressing includes a central dressing portion which may have an incision guide line, transverse index lines and intersecting grid lines which may be radio-opaque thereon, and a peripheral drape portion which portions are secured together by means of a weakened tear line. A straddling closure is utilized in conjunction with the combination drape and dressing to close an incision made through the dressing portion of the combination drape and dressing which straddling closure may be integral with or separate from the drape and dressing and extends over and beyond the entire length of the incision and for a substantial distance on both sides thereof. The straddling closure may be substantially flat or in a modification may be initially rolled, to be rolled onto the dressing portion of the combination drape and dressing over an incision therethrough. In a further embodiment, the straddling closure may be a quick air drying polymer rolled or sprayed onto the dressing portion of the combination drape and dressing over an incision therethrough. Also, the straddling closure may be constructed of stretchable material. Antiseptic material and/or medication may be sprayed on or placed in the dressing portion of the combination drape and dressing, or the straddling closure. All or any of the portions of the combination surgical drape, dressing and closure structure may be color coded for such things as medication, size and shape.

12 Claims, 3 Drawing Sheets

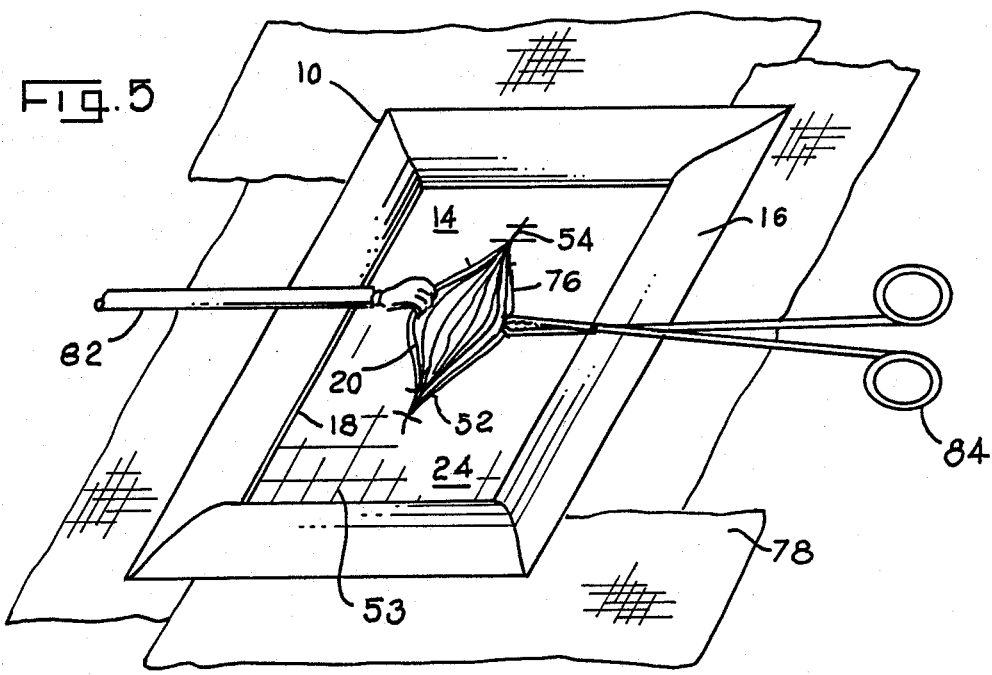
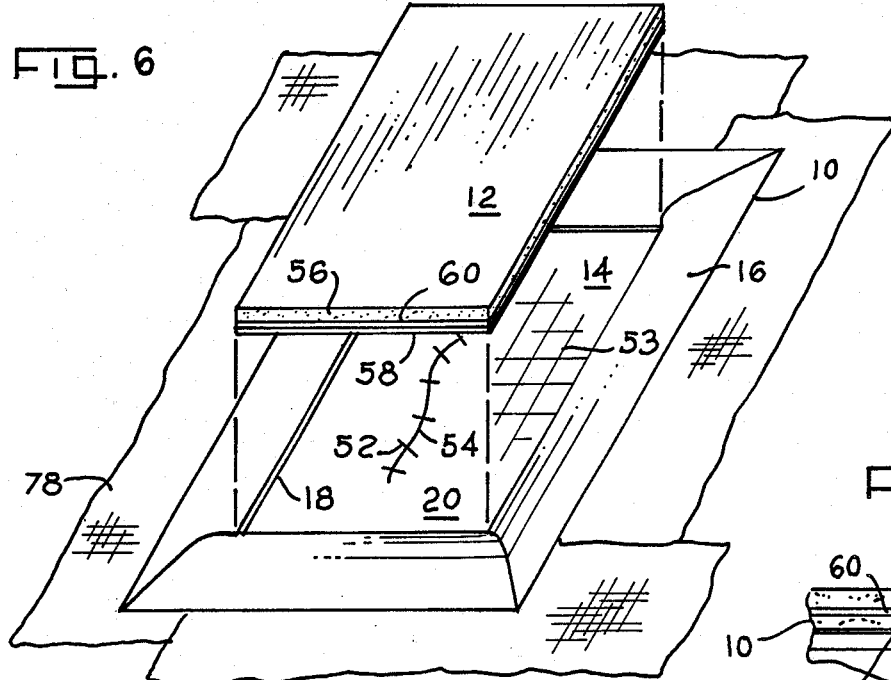
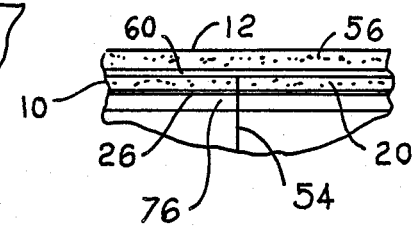
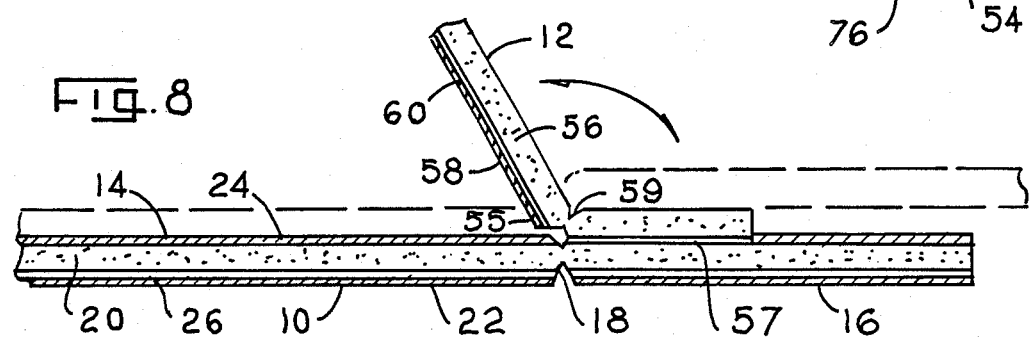

MULTI-PURPOSE INTEGRATED SURGICAL DRAPE, DRESSING, AND CLOSURE STRUCTURE AND METHOD

CROSS REFERENCE TO RELATED APPLICATIONS

This application is a continuation in-part of application Ser. No. 444,842, filed Nov. 26, 1982, which is a continuation in part of application Ser. No. 178,103, filed Aug. 14, 1980, both now abandoned.

BACKGROUND OF THE INVENTION

1. Field of the Invention

The invention relates to the combination of a surgical drape, dressing and closure into an integrated system with a separately assigned function for each section of the integrated system, it being understood that this combination surgical drape, dressing and closure is utilized before, during and after a surgical procedure.

More specifically, the surgical drape dressing and closure system of the invention includes a central dressing portion and a peripheral drape portion which are initially integrated and subsequently detachable from each other. The peripheral drape portion is assigned to towel retention. The unique flexible, transparent, translucent, or opaque, central section is adapted to adhere to a substantially flat or multi-curved clean field of skin surface through which an incision is made following a premarked target incision line that may be straight or curvilinear and marked directly on the skin, if the central section is translucent or transparent, or preferably marked on the central section itself, on a preprinted grid line pattern on the central section, if the central section, although of transparent material cannot be seen through because it is of open cell construction, i.e. is spongy, to allow medicine retention as explained later.

The central section features an integral structure of open cell foam or the like throughout its thickness, allowing the application of retractors, forceps or clamps that do not pinch the skin proper, but grab only the material of the central section at the edge of the incision. The central section stays in place on closing and functions as a dressing with medication which may be contained within its open cell foam structure and provides a base support for an integral or separately applied, alternatively perpendicularly placed or rolled on, adhering, straddling closure portion of the combination surgical drape, dressing and closure system that replaces the usual final layer of closing stitches, staples or steri-strips. Medication may also be applied to or by the straddling closure.

2. Description of the Prior Art

In prior surgical procedures, it has been the usual practice to first cleanse a surgical field, that is, the area in which an incision is to be effected. Adjacent skin areas have been draped to protect them from accidental damage from sharp instruments and the like and to localize or absorb body fluids.

During surgical procedures in the past, incisions have been retracted by retractors or clamps secured to skin tissue at the edge of the incision or within the wound. An incision made during a surgical procedure in the past, has generally been closed by stitching, stapling, or the like of the skin upper layer and a dressing has been placed over the closed incision. Drapes have been removed in past procedures before skin suture or closure as described above.

Accordingly, prior surgical structures and methods have included separate structure for and steps of cleansing the surgical field, draping the surgical field, retraction by gripping and pinching tissue which may result in damaged tissue, and subsequently closing with procedures which may damage tissue adjacent the incision and/or effect an incomplete closure of the incision and requiring separately applied medication and dressings.

Also, prior surgical closure structure and methods are slower than desirable resulting in greater fatigue of surgeons and exposure of patients to a prolonged period under an anesthetic with an open surgical incision. Further such prior methods and structures may produce more scar tissue such as clamp and stitch marks and require longer healing times than desirable. Also the chance of infection with such prior procedures is greater than necessary. No drape is currently in general use as a dressing or dressing base.

SUMMARY OF THE INVENTION

The structure of the invention includes a combination surgical drape, dressing and straddling closure. The straddling closure may be integral with or separate from the surgical drape and dressing. Means are provided for securing a dressing portion of the combination drape, dressing and straddling closure to the skin of a patient over the field of a surgical procedure, for securing a drape portion of the combination drape, dressing and straddling closure to towels surrounding the field of the surgical procedure and for securing the straddling closure over the incision after the surgical procedure is completed.

In accordance with the structure of the invention, the straddling closure may take a number of different forms. Thus the straddling closure may be a substantially flat or a developable member as the subjacent skin surface may be. Alternatively the closure structure may be provided in the form of a roll to be unrolled for adhesion over the incised skin area. The straddling closure may also be a quick air drying polymer.

The dressing portion of the combination surgical drape, dressing and straddling closure may include skin cleansing material and/or medication. Further, the straddling closure portion may include medication therein and may be color coded to designate various specific medications, dressing sizes, specialized shapes or standards. Finally a closure may be so constructed as to allow stretching it in one or more directions when applied over spheroidal skin surfaces.

In accordance with the method of the invention a surgical procedure is accomplished by placing the combination surgical drape, dressing and straddling closure over a marked area in which an incision is to be made in a patient, adhering the dressing portion to the patient over a surgical field, securing towels around the surgical field with the drape portion of the combination drape, dressing and straddling closure, effecting an incision through the dressing portion, retracting the incision with retractors, forceps or clamps secured only to the dressing portion of the combination drape, dressing and straddling closure adjacent the edges of the incision and subsequently closing the incision with the straddling closure portion of the combination drape, dressing and straddling closure extending over and beyond the entire length of the incision and also extending transversely a substantial distance on either side thereof and secured to the dressing portion.

It is understood that the surface of the skin on which the incision is premarked may be planar (flat) or developable (a surface which may be generated by a straight line into a ruled, cylindrical or conical surface) and that one of the objects of the invention is to provide a straddling closure, that when in place matches exactly said surface of the subjacent skin, i.e. is so constructed, according to the invention as to become planar (flat) or developable (ruled, cylindrical or conical) or spheroidal when stretchable to match the subjacent surface when in place.

Depending on the particular straddling closure utilized, the straddling closure may be integral with the drape and dressing portions of the combination drape, dressing and straddling closure or separate therefrom. When the straddling closure is planar and separate, it may be held in place parallel to the plane of the dressing portion and moved into surface to surface contact with the dressing portion over the entire incision, by movement generally perpendicular to the dressing portion. In the case of a rolled straddling closure portion, the straddling closure portion may be rolled onto the dressing portion of the combined drape, and dressing portion and at the same time a protective cover may be rolled off of the top of the base or body part of the dressing portion to allow the uncovered adhesive to adhere to the rolled on straddling closure. Alternatively, a quick air drying polymer material may be applied on the dressing portion after the subcutaneous tissue of the incision has bee stitched, stapled or otherwise proximated. Thus the principle combination drape, dressing and straddling closure is obtained in the course of a surgical procedure conducted according to the invention.

BRIEF DESCRIPTION OF THE FIGURES

FIG. 5 is a perspective view of the drape and dressing portion of the combination surgical drape, dressing and straddling closure structure of the invention shown in FIGS. 1 through 4 utilized in a surgical procedure and specifically illustrating an incision each edge of which is retracted in accordance with the method of the invention without pinching the skin, but only grasping the dressing material adhering to the top of the skin.

FIG. 6 is a perspective view of the drape and dressing portion of the combination surgical drape, dressing and straddling closure structure of the invention as shown in FIGS. 1 and 2 with a flat straddling closure portion in position to be applied over an incision made through the dressing portion during a surgical procedure in accordance with the method of the invention.

FIG. 7 is an enlarged partial section view of the structure shown in FIG. 6 with the straddling closure portion in position on the dressing portion of the combination drape, dressing and straddling closure structure of the invention.

FIG. 8 is a section view similar to FIG. 3 and showing an integral, flat straddling closure in position to be applied over the incision.

FIG. 10 is a section view similar to FIG. 3 and showing an integral, manually rolled straddling closure in position to be applied over the incision, the adhesive being an integral portion of the straddling closure being rolled on.

DESCRIPTION OF THE PREFERRED EMBODIMENT

Figure 9:
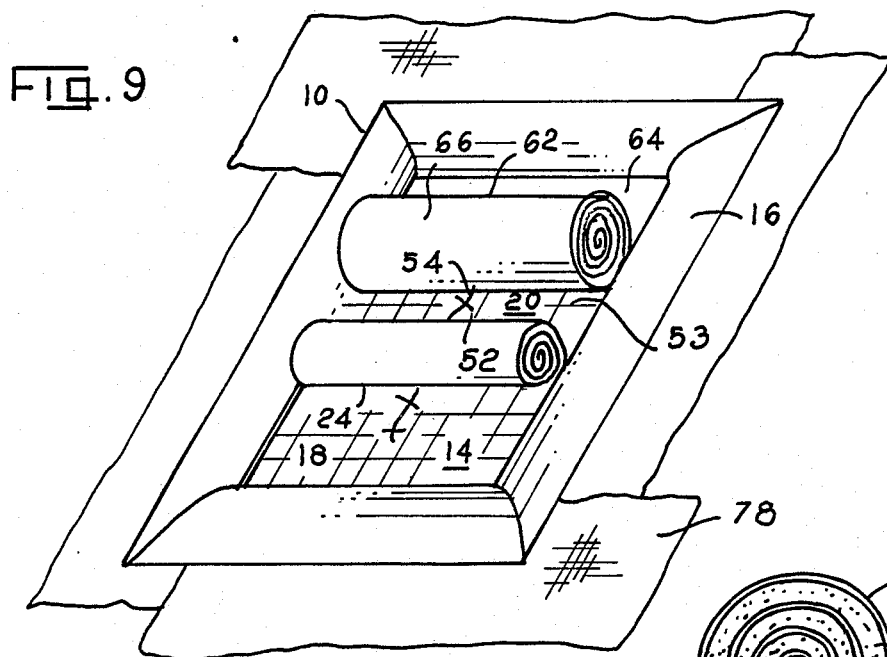
FIG. 9 is a perspective view showing a separate, manually rolled straddling closure portion in the process of being rolled over an incision previously made through the dressing portion of the combination dressing and drape while the dressing adhesive protective covering is being rolled off the dressing base in front of the rolled on closure to assure the mutual adhesion of the uncovered dressing portion and the straddling closure in accordance with the method of the invention.
Figure 10:
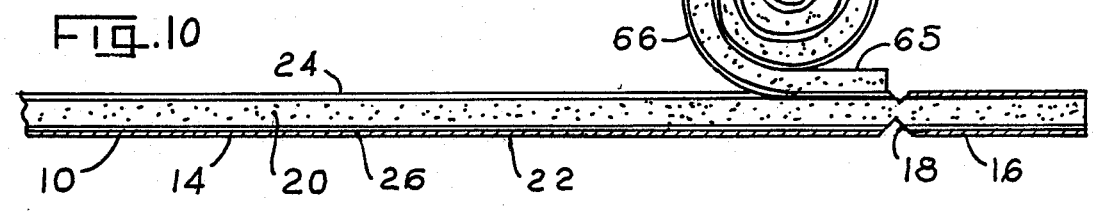
Figure 11:
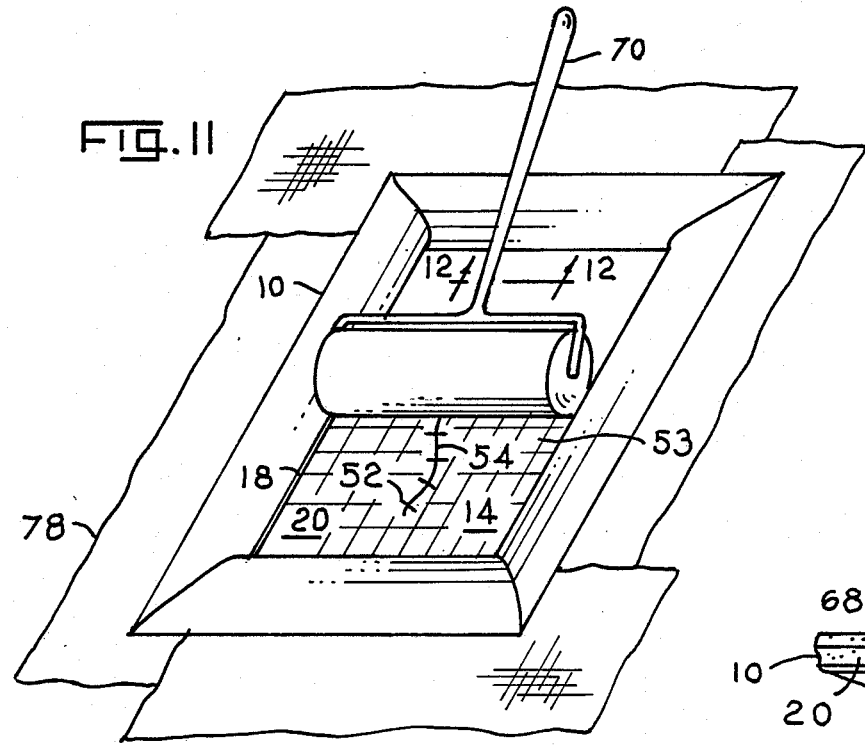
FIG. 11 is a perspective view of the combination surgical drape and dressing portion of the invention in use in conjunction with a straddling closure adhering liquid paste which is rolled on with a device in accordance with the method of the invention.

The multi-purpose surgical drape, dressing and closure structure of the invention includes a combination drape and dressing 10 as best shown in FIGS. 1 through 4 and a straddling closure 12 best shown in FIG. 6. The straddling closure 12 may be integral with, as shown in FIG. 8 and 10, or separate from, as shown in FIGS. 6, 9 and 11, the drape and dressing 10.

In accordance with the method of the invention the drape and dressing 10 and closure 12 are utilized in combination before, during and after a surgical procedure to cleanse a skin area and drape a surgical field where the incision is to take place and to assist in retraction of, closing and final dressing of the incision.

Figure 2:
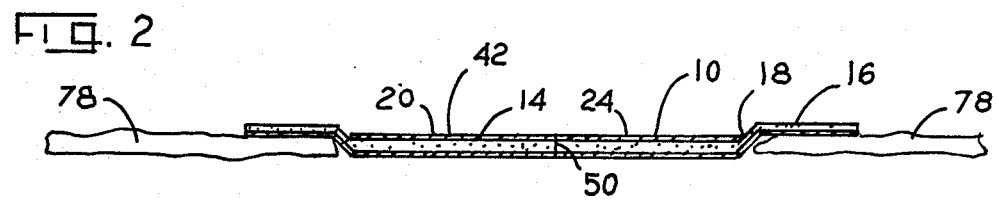
FIG. 2 is a section view of the drape and dressing portion of the combination surgical drape, dressing and straddling closure structure of the invention taken substantially on line 2—2 in FIG. 1.
Figure 3:
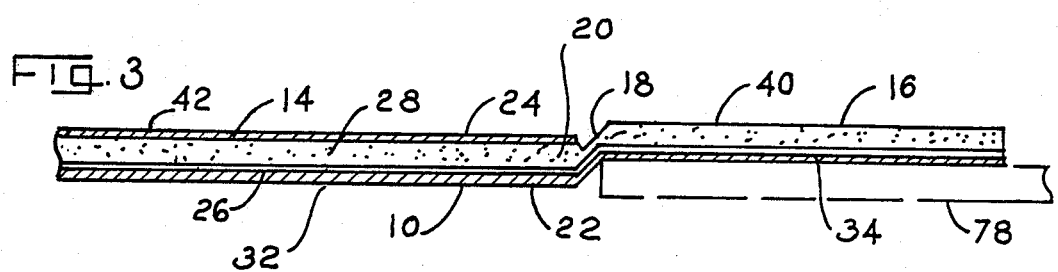
FIG. 3 is an enlarged partial section view of the drape and dressing portion of the combination surgical drape, dressing and straddling closure structure shown in FIGS. 1 and 2, also taken substantially on the line 2—2 in FIG. 1 and before the incision is performed.

More specifically the combination drape and dressing 10 as shown particularly in FIGS. 2 and 3 includes a central dressing portion 14 and a peripheral drape portion 16. The dressing portion 14 and drape portion 16 of the combination drape and dressing 10 are separated by a weakened tear line 18, weakened by known methods separately or in combination using perforations and/or a thinner cross-section along a given path and the like.

As shown in FIG. 3, both the dressing portion 14 and drape portion 16 of the combination drape and dressing 10 include a central, substantially flat, body part or base 20 constructed of an open cell polymer such as polyurethane or silicone compound which is absorbent to body fluids and is inert with respect thereto. The material of the body member 20 is non toxic and may also be biodegradable over time if desired. The body member 20, to allow it to be thick enough for grabbing by clamps, forceps, retractors and the like without their contacting subjacent skin, is perferably approximately and at least three sixteenth of an inch thick and as previously indicated is of various standardized dimensions in a single plane to accomodate different surgical field areas.

The combination drape and dressing 10 as shown in FIG. 3 further includes a bottom cover 22 and a top cover 24 that can be rolled off or otherwise removed for specific purposes as follows. Bottom cover 22 is removed to expose the adhesive 26 and allow the combination drape and dressing 10 to adhere to the skin before surgery. Top cover 24 is made of conventional slick material such as paper or plastic film to allow it to be wiped off during surgery and is removed after surgery, during closure, to allow the straddling member 12 to be applied over and become adherent to the exposed body member 20 according to the invention.

If desired the weakened tear line 18 may be extended through and around the central portion of the bottom cover 22 to facilitate exposing the underlying adhesive 26 on the center dressing portion 14 for its application over the future incision and later removal of the peripheral drape portion 16 of the combination drape and dressing 10 to allow the underlying peripheral area to retain the surgical towels throughout the surgery.

The center body member 20, as shown in FIG. 3, in a preferred embodiment, is transparent or translucent for reasons that will become apparent subsequently. Also, in another preferred embodiment, no adhesive material is positioned between the top cover 24 and the body member 20 except that necessary to secure the top cover 24 to the body member 20 until removed to receive the straddling closure that then carries the necessary adhesive to assure its attachment to body member 20.

The combination surgical drape and dressing 10 illustrated in FIG. 3 again includes a dressing portion body member 20, which may be spongy, and a bottom cover 22 having a separately detachable portion 32 and a separately detachable peripheral drape portion 34. Again adhesive 26 is provided between the body member 20 which stays on during and after surgery and central portion 32 of the bottom cover 22 which central portion is removed first prior to surgery to allow the body member 20 to be adhered to the patients skin over the incised area. Adhesive material 26 is also provided between the separately detachable peripheral drape portion 34 of the bottom cover 22, and the peripheral drape portion 40, of body member 20 which is a peripheral extension of the central dressing portion 28 of the body member 20. Again, if desired the weakened tear line 18 is provided between the dressing portion 32 and drape portion 34 of the bottom cover 22 of the combination surgical drape and dressing 10 as shown in FIG. 3. Peripheral portion 40 will adhere to towels 78 once peripheral portion 34 of the bottom cover 22 has been removed after the central section 28 is in place and adhering to a patients skin.

It will be understood that other embodiments of the combination surgical drape and dressing 10 as shown in FIG. 3 and modifications thereof are contemplated within the scope of the invention. Thus, for example, an adhesive, not shown, may be provided between the top cover 24 and the dressing portion 14 of the body 20 of the combination surgical drape and dressing 10 to secure a straddling closure thereto as will be seen subsequently.

Figure 4:
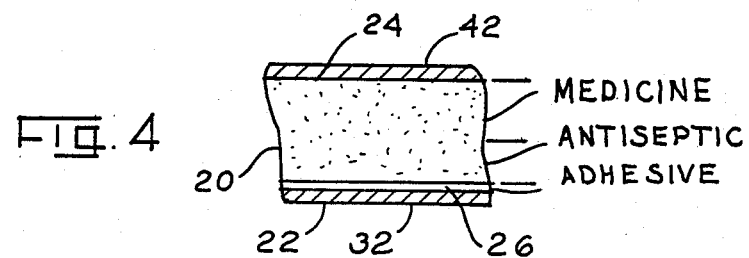
FIG. 4 is an enlarged section view of the base or body part of the drape and dressing portion of the combination surgical drape, dressing and straddling closure shown in FIGS. 1 through 3 illustrating the approximate relative location of medicine and antiseptic material therein and adhesive material thereon.

Also, in accordance with the invention, the dressing portion 14 of the combination surgical drape and dressing 10 may be impregnated with a cleansing material to prepare a surgical field skin area over which it is secured. Further, medication may be placed in the dressing portion 20 of the combination surgical drape and dressing 10 that may be, for this purpose constructed of an open cell foamed material such as a silicone or urethane. The medicine, antiseptic material and adhesive may be heterogeneous, i.e. layered as shown in FIG. 4 or homogeneous and therefore mixed uniformly within the dressing structure and are mutually compatible.

Figure 1:
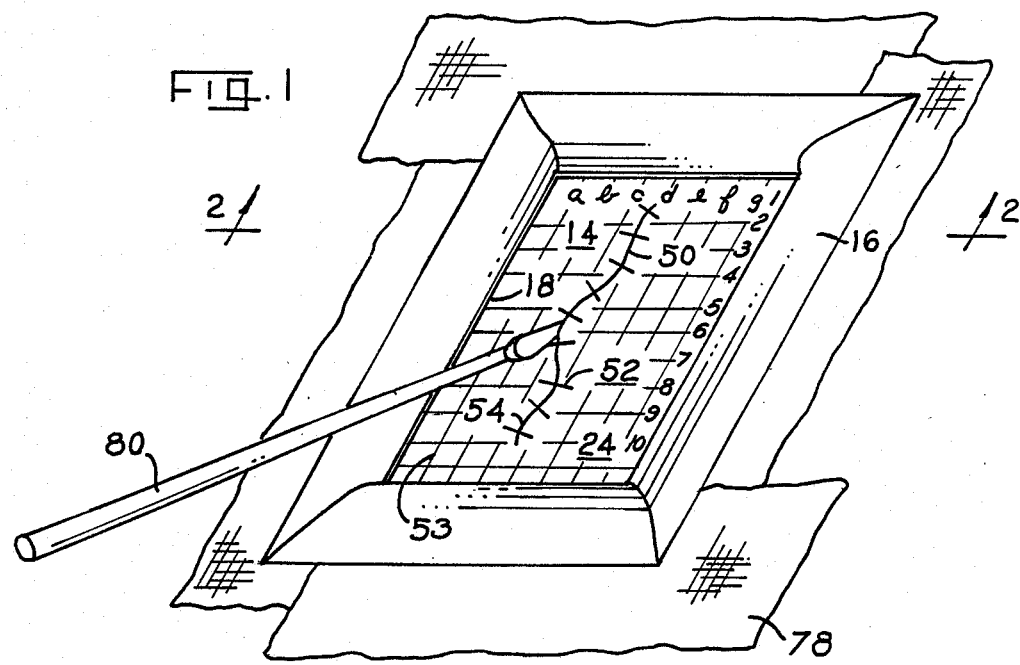
FIG. 1 is a perspective view of the drape and dressing portion of the combination surgical drape, dressing and straddling closure structure of the invention for accomplishing a surgical procedure in accordance with the method of the invention showing it in use during a surgical procedure. The more general curvilinear incision marking is shown over a preprinted reference grid line arrangement with a scalpel blade severing the skin surface, without the surgeons hand holding the scalpel being shown.

As shown in FIG. 1, incision guide line 50 may be traced by the surgeon on the top cover 24 that may also carry preprinted grid lines 53 that may also appear on the underlying top surface of the dressing portion 28 of body member 20. The grid lines 53 may be radio-opaque (i.e. of a material opaque to x-rays). Index lines 52 traced by the surgeon across the intended incision line 50 may also be provided on the top surface of the dressing portion of the body member of the combination surgical drape and dressing 10 and/or on the top cover 24 as desired to facilitate alignment of the edges of an incision 54 as shown in FIG. 1. Also, alternately if the body portion 20 and top cover 24 of the dressing portion 14 of the combination drape and dressing 10 are transparent or sufficiently translucent, the incision guide line 50, the index line 52 and the grid line 53 may be traced on a patients skin prior to adhering the combination surgical drape and dressing thereto after removal of bottom cover 32.

The straddling closure 12 as shown in FIGS. 6 and 7 is a separate, substantially flat member which again may include a body portion 56 and lower cover 58 for protecting a layer of adhesive material 60 positioned between the body portion 56 and lower cover 58. The material of the body portion 56 and the bottom cover 58 may be the same as the material of the body portion 20 and the bottom cover 22 of the combination drape and dressing 10.

The straddling closure 12 may be of any necessary size to cover the incision 54 extending over and beyond the entire length of the incision and extending also transversely a substantial distance on either side of the incision 54. Medication may be placed in the straddling closure 12 as desired to supplement or react with the medication embedded in the central portion of the base 20.

As shown in FIG. 8, and assuming a generally planar or developable surgical field (most of the cases), the straddling closure 12 may be secured at one edge 55 to the combination drape and dressing 10 by convenient means such as adhesive 57 so as to be integral therewith. In use the integral flat straddling closure 12 is folded about fold line 59 away from the dressing portion 14 of the combination drape and dressing 10 during a surgical procedure. After a surgical procedure the top cover of the dressing portion 14 of the combination drape and dressing 10 is removed along with the bottom cover 58 of the straddling closure 12 to expose the adhesive 60. The straddling closure 12 is then folded about the one edge 55 along fold line 59 and adhered to the dressing portion 14 of the combination drape and dressing 10 as before. If the skin surface is generally a ruled, developable surface (thigh, abdomen etc.), line 59 should be located along a linear feature of the skin.

The modified separate, straddling closure 62 shown in FIG. 9 again includes a prerolled body member 64 having an adhesive material 66 on the lower surface thereof. The straddling closure 62 is initially prerolled with the adhesive bottom surface on the outside of the roll in the manner of a reversely rolled, cellophane tape or preglued wall paper rolls. A protective bag or cover (not shown) is initially placed over the adhesive structure of the prerolled, separate, straddling closure 62. Alternatively a protective cover may initially be applied along the total external surface of the straddling closure 62 and progressively rolled off as 62 is rolled on the central portion of the dressing base 20. Again medication may be placed in the body member 64 as designed since its alternate and preferred open foam construction will so permit.

Again, as shown in FIG. 10 the rolled straddling closure 62 may be initially secured at one end 65 to the combination drape and dressing 10 so as to be integral therewith in that area.

Figure 12:
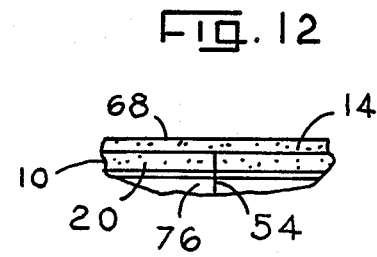
FIG. 12 is a section view through the combination surgical drape and dressing portion of the invention in use in conjunction with the rolled on straddling closure shown in FIG. 11 taken substantially on the line 12—12 in FIG. 11.

Also, the modified straddling closure 68 shown in FIGS. 11 and 12 is a quick drying polymer paste, such as polyurethane or a silicone and is rolled onto the dressing portion 14 of the body member 20 of the combination dressing and drape 10 over the incision 54 by means of the roller 70.

In accomplishing a surgical procedure in accordance with the method of the invention, with the structure of the invention as described above and particularly with respect to the embodiment of the combination dressing and drape 10 shown in FIGS. 1 through 7, the combination surgical dressing and drape 10 is selected of a size for a particular surgical procedure to include medicine and antiseptic material in the dressing portion 14 of the body member 20 thereof. The incision guide line 50, and index lines 52 are on the body member 20 beneath a transparent top cover 24, as are the preprinted grid lines 53.

The bottom cover 22 of at least the dressing portion of the bottom cover 22 is removed from the body member 20 with the aid of the weakened tear line 18 if desired and the combination surgical dressing and drape 10 is adhered to the skin 76 of a patient over a surgical field wherein an incision is required. The surgical field is presterilized and/or is cleansed by means of the antiseptic material carried in the dressing portion of the body member 20 of the combination surgical dressing and drape 10.

Draping of the patient is completed by placing surgical towels 78 around the surgical field and securing them to the peripheral drape portion 16 of the combination surgical dressing and drape 10 by removing the peripheral drape portion 34 of the bottom cover 22 to expose the adhesive material 26 on the bottom surface of the peripheral drape portion 34 of the body member 20 to which the towels are adhered.

An incision in the patient is effected by means of a scalpel 80 as shown in FIG. 1, along the incision guide line 50 drawn on the body member or base 20.

During the surgical procedure the incision 54 may be retracted by a retractor 82 or forceps 84 or conventional clamps (not shown) secured only to the combination surgical dressing and drape 10 at the edges of the incision and not to the patients skin tissue as particularly shown in FIG. 5. Thus, minimal damage is caused to tissue surrounding the incision during retraction of the incision in accordance with the method of the invention since the localized pulling force of, say, the forceps is redistributed and lowered over a larger area of the subjacent skin through the adhesive and dressing means.

Further, in accordance with the method of the invention, during the surgical procedure, the relatively slick non-absorbent drape portion 16 of the combination surgical dressing and drape 10 permits easy wiping of body fluids and debris in and around the surgical field.

After the surgical procedure is accomplished the edges of the incision 54 are aligned with the aid of the index lines 52 and or the grid lines 53, and the incision is closed with a straddling closure 12 as shown in FIG. 6 or other straddling closure such as the straddling closures 62 and 68 shown in FIGS. 9 and 11 which have been preselected of a desired size to completely cover the incision over and beyond the entire length thereof and to extend for a substantial distance on each side of the incision.

In closing the incision 54 with the straddling closure 12, the bottom cover 58 is stripped therefrom to expose the adhesive material 60 and the body portion 56 of the straddling closure 12 is moved over the incision as shown in FIG. 6 to be substantially parallel with the plane of the dressing portion 14 of the combination drape and dressing 10 and in spaced apart relation thereto. The straddling closure 12 is then moved substantially perpendicularly to the combination dressing and drape 10 and is adhered to the dressing portion 14 thereof over and beyond the entire length of the incision and for a substantial distance on both sides thereof.

With such closure of the incision no damage is done to the edges of the incision as would occur with stitching and/or stapling and the edges of the incision are perfectly aligned and abutted and no eversion thereof is permitted whereby the incision should heal faster and with less scarring than with prior closing procedures. The closed incision is illustrated in FIG. 7.

Alternatively, as shown in FIG. 9, if a rolled straddling closure 62 is selected, the straddling closure 62 is rolled onto the dressing portion 14 of the combination dressing and drape 10. The top cover 24 of the dressing portion 14 of the combination surgical dressing and drape 10 must be similtaneously rolled off of the body member 20 of the dressing portion 14 of the combination dressing and drape as the closure 62 is rolled on as shown in FIG. 9.

The roll on and roll off straddling closure and top cover as shown in FIG. 9 have the advantage of particularly short exposure time for the top surface of the dressing portion 14 of the body member 20 and may be easier for the surgeon in closing long incisions.

In the closing procedure shown in FIG. 11, it is contemplated that the incision 54 first be closed by conventional stitching, stapling or the like. The straddling closure 68 then acts as an additional closure for the incision and completely seals the incision. As set forth above, any of the straddling closures can be caused to provide medication to aid in the healing of the incision.

Following the closure of the incision the drape portion 16 of the combination dressing and drape 10 may be removed along with the surgical towels at the weakened tear line 18 to effect a finished surgical procedure. It will be particularly noted that the structure of the invention has been utilized prior to the actual surgical incision, during the surgical procedure and subsequent to the closure of the incision.

While different embodiments of the invention have been set forth in detail along with modifications thereof, it will be understood that other embodiments and modifications of the invention are contemplated.

Thus, for example, the antiseptic material and medication may be sprayed on the dressing or straddling closure instead of being placed therein. Similarly, the pasty liquid, quick drying polymer, straddling closure 68 may be sprayed on instead of being rolled on. The rolled straddling closure 66 as shown in FIG. 9 may also be applied with a roller including a handle such as that of device 70 shown in FIG. 11. Further the combination surgical drape, dressing and straddling closure of the invention may be color coded to indicate specific medication, size, shape or other specific structure, function or use as desired.

It is the intention to include all such embodiments and modifications and various combinations thereof as are defined by the appended claims within the scope of the invention.

I claim:

1. A combination surgical drape and dressing for use before, during and after a surgical procedure comprising a central dressing portion for defining a surgical field, a peripheral drape portion extending around the periphery of but not over the central dressing portion connected only to the periphery of the dressing portion for securing surgical towels to the combination surgical drape and dressing, an adhesive on one side of the dressing portion of the combination surgical drape and dressing for securing the dressing portion to the skin of a patient in which an incision is to be made and an adhesive on at least one side of the drape portion of the combination surgical drape and dressing for securing the towels in position around the surgical field, and further including a target tracing of the future incision to be performed, and at least one of index marks transverse to the target tracing or preprinted intersecting grid lines on a protective cover or the top surface of the dressing portion of the combination surgical drape and dressing for facilitating making of an incision and alignment of the edges of an incision made through the dressing portion on closing of the incision wherein the preprinted grid lines are radio opaque.

2. A combination surgical drape and dressing, for use before, during and after a surgical procedure comprising a central dressing portion for defining a surgical field, a peripheral drape portion extending around the periphery of but not over the central dressing portion connected only to the periphery of the dressing portion for securing surgical towels to the combination surgical drape and dressing, an adhesive on one side of the dressing portion of the combination surgical drape and dressing for securing the dressing portion to the skin of a person in which an incision is to be made, and an adhesive on at least one side of the drape portion of the combination surgical drape and dressing for securing the towels in position around the surgical field and a single straddling closure extending over the central dressing portion of the combination surgical drape and dressing covering the entire length of an incision and beyond made through the dressing portion and also extending transversely and substantially beyond the edges of the incision on both sides thereof and secured to the dressing portion of the combination surgical drape, dressing and straddling closure wherein the straddling closure is rolled with that side of the closure intended to contact the dressing portion of the combination drape and dressing on the outside of the roll so as to be rolled onto the dressing portion of the combination drape and dressing to close an incision made through the dressing portion and to further include means on at least one of the straddling closure and the dressing portion of the combination drape and dressing for securing the straddling closure to the dressing portion over the incision.

3. A combination surgical drape and dressing, for use before, during and after a surgical procedure comprising a central dressing portion for defining a surgical field, a peripheral drape portion extending around the periphery of but not over the central dressing portion connected only to the periphery of the dressing portion for securing surgical towels to the combination surgical drape and dressing, an adhesive on one side of the dressing portion of the combination drape and dressing for securing the dressing portion to the skin of a patient in which an incision is to be made and an adhesive on at least one side of the drape portion of the combination surgical drape and dressing for securing the towels in position around the surgical field and a single straddling closure extending over the central portion of the combination surgical drape and dressing covering the entire length of an incision and beyond made through the dressing portion and also extending transversely and substantially beyond the edges of the incision on both sides thereof and secured to the dressing portion of the combination surgical drape, dressing and straddling closure wherein the straddling closure is a quick air drying polymer paste rolled onto the dressing portion of the combination drape and dressing to cover an incision made through the dressing portion.

4. Closure structure for a surgical incision comprising a dressing extending substantially the length of an incision and on each side and completely up to the edge of the incision and a single piece straddling closure extending over the full length of the incision on both sides of the incision and means for securing the straddling closure to the dressing, wherein the dressing is substantially flat and the straddling closure is initially prerolled with the surface intended to contact the surface of the dressing on the outside of the roll to permit the unrolling of the straddling closure onto the dressing.

5. Closure structure for a surgical incision comprising a dressing extending substantially the length of the incision and on each side and completely up to the edge of an incision and a single piece straddling closure extending over the whole length of the incision and on both sides of the incision and means for securing the straddling closure to the dressing wherein the straddling closure is a rolled on polymer base material.

6. A surgical drape and dressing method comprising placing a combination drape and dressing including a central dressing portion and a drape portion only peripherally attached to the dressing portion over an area where a surgical procedure is to be performed, adhering the dressing portion of the combination drape and dressing over the area where the surgical procedure is to be performed, and securing towels to the peripheral drape portion of the combination surgical drape and dressing around the area where the surgical procedure is to be performed, closing an incision through the dressing portion of the combination drape and dressing by placing a straddling closure over and beyond the length of the incision over the entire length of the incision and extending transversely for a substantial distance on both sides of the incision and securing the straddling closure to the dressing portion of the combined surgical drape and dressing wherein the straddling closure is prerolled initially with the portion intended to engage the dressing on the outside of the roll and further including the step of unrolling the straddling closure onto the dressing portion of the combined drape and dressing and over the incision therethrough.

7. The method as set forth in claim 6 and further including the step of rolling off a cover from the dressing portion of the combination drape and dressing as the straddling closure is rolled onto the dressing portion to facilitate adhesion of the straddling closure onto the dressing portion.

8. A surgical drape and dressing method comprising placing a combination drape and dressing including a central dressing portion and a drape portion only peripherally attached to the dressing portion over an area wherein the surgical procedure is to be performed, adhering the dressing portion of the combination drape and dressing over the area where the surgical procedure is to be performed and securing towels to the peripheral drape portion of the combination surgical drape and dressing around the area where the surgical procedure is to be performed and closing an incision through the dressing portion of the combination drape and dressing by placing a straddling closure over and beyond the length of the incision over the entire length of the incision and extending transversely for a substantial distance on both sides of the incision and securing the straddling closure to the dressing portion of the combined drape and dressing wherein the straddling closure is formed of a quick air drying polymer paste and further including the step of rolling the quick air drying polymer onto the dressing portion of the combination surgical drape and dressing.

9. A combination surgical drape and dressing, for use before, during and after a surgical procedure comprising a central generally rectangular portion defining a surgical field, a drape portion extending around the periphery of the dressing portion which is generally rectangular in outline and which is integrally connected to the dressing portion around the outer periphery of the dressing portion by a weakened tear line and does not extend over the central dressing portion, an adhesive on the bottom of the dressing portion and bottom of the drape portion of the combination drape and dressing, a bottom cover over the adhesive on the bottom of both of the central dressing portion and drape portion of the combination drape and dressing, and a top cover over the dressing portion of the combination surgical drape and dressing, and a rolled closure member adapted to be rolled onto the dressing portion of the combination drape and dressing member for closing an incision made through the dressing portion thereof having the surface intended to engage the dressing portion of the combination drape and dressing member on the exterior thereof.

10. A combination surgical drape and dressing member for use before, during and after a surgical procedure comprising a central generally rectangular dressing portion defining a surgical field, a drape portion extending around the periphery of the dressing portion which is generally rectangular in outline and which is integrally connected to the dressing portion around the outer periphery of the dressing portion by a weakened tear line and which does not extend over the central dressing portion, an adhesive on the bottom of the dressing portion and bottom of the drape portion of the combination surgical drape and dressing, a bottom cover over the adhesive on both the central dressing portion and drape portion of the combination surgical drape and dressing, a top cover over the dressing portion of the combination surgical drape and dressing and a closure paste for closing an incision through the dressing portion of the combination drape and dressing member on being rolled onto the top of the dressing portion of the combination drape and dressing member.

11. A combination surgical drape and dressing, for use before, during and after a surgical procedure comprising a central dressing portion for defining a surgical field, a peripheral drape portion extending around the periphery of but not over the central dressing portion connected only to the periphery of the dressing portion for securing surgical towels to the outer periphery of the drape portion of the combination surgical drape and dressing, an adhesive on one side of the dressing portion of the combination surgical drape and dressing for securing the dressing portion to the skin of a patient in which in incision is to be made, an adhesive on at least one side of the drape portion of the combination surgical drape and dressing for securing the towels in position around the surgical field, and a target tracing of the future incision to be performed, and at least one of index marks transverse to the target tracing or preprinted intersecting grid lines on either a protective cover or the top surface of the dressing portion of the combination surgical drape and dressing for facilitating making of an incision and alignment of the edges of an incision made through the dressing portion upon closing of the incision.

12. A surgical drape and dressing method comprising placing a combination drape and dressing over an area wherein a surgical procedure is to be performed, adhering a dressing portion of the combination drape and dressing over the area where the surgical procedure is to be performed, securing towels to a peripheral drape portion of the combination surgical drape and dressing around the area where the surgical procedure is to be performed, and aligning the opposite sides of an incision made through the dressing portion of the drape and dressing on closing of the incision by aligning index marks or pre-printed grid lines on the dressing portion of the combined surgical drape and dressing, at the edges of the incision.

* * * * *